United States Patent [19]

Parks et al.

[11] Patent Number: 4,999,582

[45] Date of Patent: Mar. 12, 1991

[54] BIOSENSOR ELECTRODE EXCITATION CIRCUIT

[75] Inventors: Robert A. Parks, Springport; Bradley E. White, Zionsville, both of Ind.

[73] Assignee: Boehringer Mannheim Corp., Indianapolis, Ind.

[21] Appl. No.: 451,108

[22] Filed: Dec. 15, 1989

[51] Int. Cl.$^5$ ............................................. G01R 27/02
[52] U.S. Cl. ................................. 324/438; 204/406; 324/444; 324/538; 324/603; 324/692; 340/568; 422/82.02
[58] Field of Search ............... 324/425, 438, 439, 603, 324/692, 693, 525, 538, 530, 537, 500, 158 R, 158 P, 601, 444, 450, 71.1; 340/568; 204/406; 422/58, 82.02, 82.01

[56] References Cited

U.S. PATENT DOCUMENTS

| | | | |
|---|---|---|---|
| 4,123,701 | 10/1978 | Josefsen et al. | 324/692 X |
| 4,178,543 | 12/1979 | Wrinn et al. | 324/421 X |
| 4,301,414 | 11/1981 | Hill et al. | 324/446 |
| 4,714,874 | 12/1987 | Morris et al. | 324/601 |

FOREIGN PATENT DOCUMENTS

| | | |
|---|---|---|
| 0230472 | 8/1987 | European Pat. Off. . |
| 250374 | 10/1987 | Japan ............. 324/538 |
| WO89/08713 | 9/1989 | PCT Int'l Appl. . |

*Primary Examiner*—Reinhard J. Eisenzopf
*Assistant Examiner*—Robert W. Mueller
*Attorney, Agent, or Firm*—Perman & Green

[57] ABSTRACT

A circuit is described for applying a potential to an electrode of a biosensing test cell, which electrode, when properly inserted in a female connector, is contacted by a pair spaced apart contacts. The circuit includes a source of excitation potential and an operational amplifier having one input connected to the source of excitation potential. A switching circuit is coupled between the operational amplifier and a first one of the spaced apart contacts, with the switch means exhibiting an impedance. A feedback circuit is connected between the second of the spaced-apart contacts and another input to the operational amplifier, to feed back a potential appearing at the second contact. The feedback is for the purpose of maintaining the output of the operational amplifier at a level which compensates for impedance losses in the swtiching circuit. The feedback circuit enables the output of the operational amplifier to be varied so that the potential applied to the electrode is equal to the source of excitation potential. A further circuit is connected to the feedback circuit for sensing when an open or high impedance state exists between the spaced-apart contacts.

6 Claims, 1 Drawing Sheet

BIOSENSOR ELECTRODE EXCITATION CIRCUIT

FIELD OF THE INVENTION

This invention relates to biosensing cells and more particularly, to a circuit for reliably energizing an electrode in a biosensing cell and assuring that the electrode is properly connected.

REFERENCE TO RELATED APPLICATIONS

This invention is related to inventions described in:
U.S Pat. application Ser. No. 07/451,107, filed Dec. 15, 1989, entitled "Regulated Bifurcated Power Supply" by Parks and White.
U.S. Pat. application Ser. No. 07/451,212, filed Dec. 15, 1989, entitled "Analog to Digital Convertion With Noise Reduction" by Parks.
U.S Pat. application Ser. No. 07/451,309, filed Dec. 15, 1989, entitled "Biosensing Instrument and Method: by White.

BACKGROUND OF THE INVENTION

Biosensing instruments for detecting analyte concentrations (e.g. glucose and cholesterol) are known in the prior art. Recently, an amperometric biosensor has appeared for measuring glucose concentrations in blood samples. In European Patent Application 0 230 472 to Nankai et al. and in PCT Published Application WO 89/08713 to Pottgen et al., amperometric techniques for determining glucose concentration are disclosed. Each system is dependent upon a reaction wherein glucose, in the presence of an enzyme, e.g., glucose oxidase, catalyzes a reaction of potassium ferricyanide to potassium ferrocyanide. After that reaction has completed, a voltage applied across the reaction zone causes the reaction to reverse with an accompanying generation of a small, but measurable, current. That current is termed the Cottrell current and, in dependence upon the concentration of glucose in the reaction zone, will follow a predetermined curve during the reverse reaction. A reading of the Cottrell current can then be converted into an indication of glucose concentration.

A number of problems exist in amperometric biosensors which employ the Cottrell current to provide an indication of an analyte concentration. As above indicated, the forward reaction must initially be allowed to proceed to completion before being reversed by an application of a voltage to electrodes which span the reaction zone. Thus, provision must be made to enable the on/off switching of a known excitation potential across the reaction zone. Without a known voltage being applied, current reading accuracies cannot be assured. Furthermore, since biosensors for determining the concentration of analytes such as glucose and cholesterol are often destined for home use, provision must be made for unskilled use of the instrument.

Accordingly, it is an object of this invention to provide a voltage excitation circuit for an amperometric biosensor which enables a potential applied to the biosensing cell to be accurately determined.

It is a further object of this invention to provide a biosensing excitation circuit which provides a clear indication when a test cell is either improperly inserted or not inserted in the biosensing instrument.

SUMMARY OF THE INVENTION

A circuit is described for applying a potential to an electrode of a biosensing test cell, which electrode, when properly inserted in a female connector, is contacted by a pair spaced apart contacts. The circuit includes a source of excitation potential and an operational amplifier having one input connected to the source of excitation potential. A switching circuit is coupled between the operational amplifier and a first one of the spaced apart contacts, with the switch means exhibiting an impedance. A feedback circuit is connected between the second of the spaced-apart contacts and another input to the operational amplifier, to feed back a potential appearing at the second contact. The feedback is for the purpose of maintaining the output of the operational amplifier at a level which compensates for impedance losses in the switching circuit. The feedback circuit enables the output of the operational amplifier to be varied so that the potential applied to the electrode is equal to the source of excitation potential. A further circuit is connected to the feedback circuit for sensing when an open or high impedance state exists between the spaced-apart contacts.

DETAILED DESCRIPTION OF THE INVENTION

Figure 1:
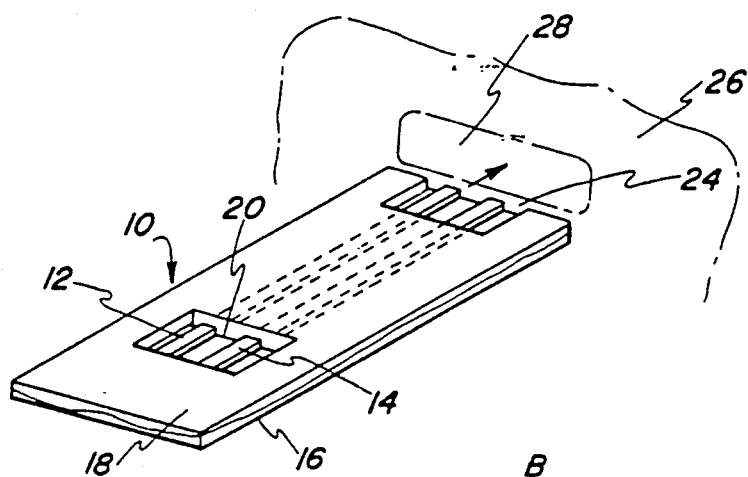
FIG. 1 is a diagram of a biosensing test cell employed with this invention, illustrating its mode of insertion into a female connector.

Referring now to FIG. 1, test cell 10 comprises a pair of electrodes 12 and 14 which are supported on a polymeric sheet 16. A cover sheet 18 is provided with openings 20 and 24 which expose conductors 12 and 14. Opening 20 creates a well and defines a reaction zone between conductors 12 and 14. A gel-like layer (not shown) of reactants overlays conductors 12 and 14 and provides a substrate on which a subsequent analyte-containing fluid sample can be emplaced.

Figure 2:
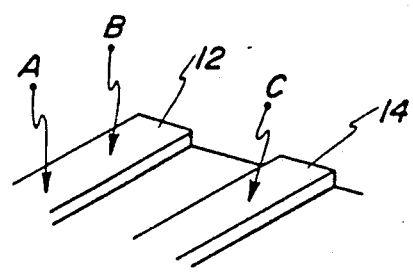
FIG. 2 is an expanded view of one end of the test cell, indicating where its electrodes are contacted by contacts within the female connector.

A face 26 of the biosensing instrument 26 is schmatically shown having an opening 28 in which a female connector is positioned. As shown in FIG. 2, when test cell 10 is inserted in opening 28, connections are made to electrodes 12 and 14 at points A, B, and C by contacts in the female connector. After test cell 10 is inserted so that contacts A, B, and C are made, a sample of fluid containing an analyte to be measured, is placed in opening 20 and the forward reaction commences between the analyte and reactants in the reaction zone. During this period, no voltage is applied to electrodes 12 and 14 and the forward reaction proceeds to completion. Then, a potential is applied to terminal B to cause a reversal of the reaction. A reading is then taken of current flow between electrodes 12 and 14.

Figure 3:
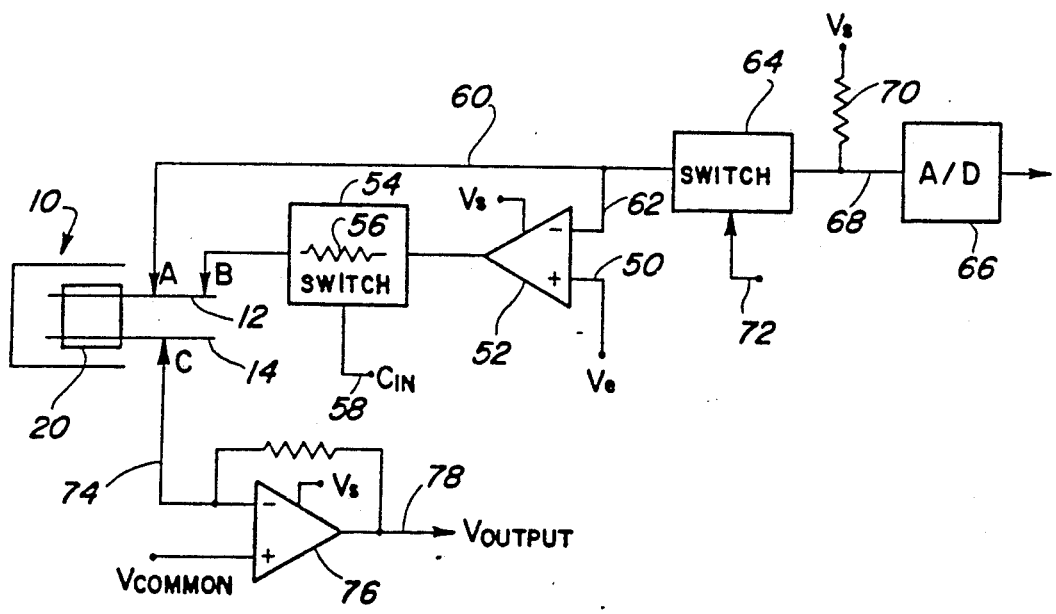
FIG. 3 is a circuit diagram of the biosensing excitation circuit.

The circuit for applying excitation to electrodes 12 and 14 is shown in FIG. 3. Test cell 10 is schematically indicated therein, with contacts A, B, and C connected to electrodes 12 and 14. An excitation potential Ve is applied to a non-inverting input 50 of operational amplifier 52. A supply voltage Vs provides the necessary biasing for amplifier 52 and exceeds the level of Ve. The output of operational amplifier 52 is fed via switch 54 to contact B and thence to electrode 12. Switch 54 exhibits an internal impedance 56 (schematically shown) which is inserted in the circuit when control line 58 causes switch 54 to close and connect the output of operational amplifier 52 to contact B.

Contact A is connected, via conductor 60, back to an inverting input 62 of operational amplifier 52 and forms a feedback circuit which assures a circuit gain of unity. Conductor 60 is also connected via a switch 64 to an analog to digital convertor circuit 66 via conductor 68. Also connected to conductor 68, via high impedance resistor 70, is a supply voltage Vs. The closed or open state of switch 64 is controlled by an input applied via conductor 72.

As above-stated, no voltage is applied to electrodes 12 or 14 during the forward reaction time. At the termination of the forward reaction, a voltage is applied to electrode 12 which enables a current to be developed between electrodes 12 and 14. That current is fed via conductor 74, to operational amplifier 76, where it is converted to a corresponding voltage and then provided as an output on conductor 78.

To apply the excitation voltage to terminal B, a control potential is applied via line 58 to cause switch 54 to close (thereby inserting its characteristic impedance between the output of operational amplifier 52 and terminal B). The excitation voltage Ve applied to non-inverting input 50 of operational amplifier 52, causes the application of a voltage to terminal B which is diminished somewhat by the drop across impedance 56. Assuming that electrode 12 is properly inserted between contacts A and B, the voltage at contact B is fed back via contact A and conductor 60 to inverting input 62 of operational amplifier 52. As a result, the output of operational amplifier 52 increases towards the value of supply voltage Vs. When the feedback voltage on line 60 eventually equals excitation voltage Ve, the circuit stabilizes and the output of operational amplifier 52 is maintained at the level necessary to assure the continued application of Ve to contact B. A current thus flows between electrodes 12 and 14 and is sensed by operational amplifier 76 and converted into a corresponding output voltage on conductor 78.

The insertion into the feedback circuit of contacts A and B, enables that circuit to also be employed to determine whether test cell 10 has been properly inserted into the biosensing instrument. If test cell 10 is improperly inserted so that electrode 12 does not make proper connection to both contacts A and B, the feedback circuit is interrupted. It can also be seen that if, for some reason, corrosion or contaminants exist which impede current flow between contacts A and B, a high impedance will occur therebetween and also cause an aberration in the feedback circuit. In either case, the level of feedback voltage applied to inverting input 62 will be greatly decreased from that which is required.

To determine that a proper voltage is being fed back, control line 72 closes switch 64 to thereby connect conductor 68 to inverting input 62 of operational amplifier 52. The closure of switch 64 also connects the supply voltage Vs (via high impdance 70) into the feedback circuit.

If a proper voltage (i.e. Ve) is being fed back on line 60, to operational amplifier 52, then the potential on line 68 will be clamped to that level, and A to D convertor 66 will provide an output indicating that the proper excitation voltage (Ve) is being applied to electrode 12. On the other hand, if when switch 64 closes, a high impedance exists between contacts A and B, the potential on line 68 will rise towards Vs when switch 64 closes causing A to D convertor 66 to provide an output indicative of a problem state. (Obviously, the output of A to D converter 66 is only sampled to provide a control indication when switch 64 is closed.) Appropriate remedial action can then be taken by the control circuitry to prevent erroneous measurements.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

We claim:

1. A circuit for applying a potential to a biosensing electrode, said electrode, when properly inserted in a connector, contacted by a pair of spaced-apart contacts, the combination comprising:

operational amplifier means having a pair of inputs and an output, one input connected to an excitation potential;

switch means coupled between said operational amplifier means and a first of said contacts, said switch means exhibiting an internal impedance;

feedback circuit means connected between a second of said contacts and a second input to said operational amplifier means, to feed back the potential at said second contact to said second input, whereby the output of said operational amplifier means is maintained at a level which compensates for a potential drop across said switch means and applies to said first contact a potential bearing a predetermined relationship to said excitation potential.

2. The circuit of claim I where a high impedance between said spaced-apart contacts causes an alteration in feedback potential on said feedback circuit means, the combination further comprising:

signal means connected to said feedback circuit means for signalling the presence of said altered feedback potential, to indicate a malfunction with respect to said circuit.

3. The circuit of claim 2 wherein said signal means comprises:

a supply voltage;

a high impedance connected to said supply voltage;

switch means for connecting said high impedance to said feedback circuit means; and sense means for indicating a problem state in response to a potential at said switch means whose value is near said supply voltage, thus indicating the presence of a high impedance between said first and second contacts.

4. The circuit of claim 3 wherein said operational amplifier means is provided with inverting and non-inverting inputs, and said feedback circuit means is a direct connection between said second contact and said inverting input.

5. The circuit of claim 4 wherein said electrode comprises one electrode of a two electrode pluggable test cell, a current detector being connected to the other electrode of said pluggable test cell.

6. The circuit as defined in claim 5 wherein said pluggable test cell includes a reaction zone connecting said electrodes and enabling a current to flow therebetween in the presence of an analyte.

* * * * *